(12) United States Patent
Zajac (10) Patent No.: US 8,076,475 B2
(45) Date of Patent: Dec. 13, 2011

(54) PROCESS

(75) Inventor: Matthew Allen Zajac, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/921,199

(22) PCT Filed: Mar. 6, 2009

(86) PCT No.: PCT/US2009/036261
§ 371 (c)(1),
(2), (4) Date: Sep. 7, 2010

(87) PCT Pub. No.: WO2009/111679
PCT Pub. Date: Sep. 11, 2009

(65) Prior Publication Data
US 2011/0015390 A1   Jan. 20, 2011

Related U.S. Application Data

(60) Provisional application No. 61/034,344, filed on Mar. 6, 2008.

(51) Int. Cl.
*C07D 401/00* (2006.01)

(52) U.S. Cl. .................................................. 540/523
(58) Field of Classification Search ................. 540/523
See application file for complete search history.

(56) References Cited

U.S. PATENT DOCUMENTS

| 2003/0050493 A1 | 3/2003 | Peters et al. ..................... 556/7 |
| 2006/0194786 A1 | 8/2006 | Conde et al. ............. 514/212.07 |

*Primary Examiner* — Bruck Kifle
(74) *Attorney, Agent, or Firm* — Grace C. Hsu; John Lemanowicz

(57) ABSTRACT

The present invention generally relates to a novel process for preparing vitronectin receptor antagonist compounds having a benzodiazepinyl core structure. This invention relates to the preparation of pharmaceutically active compounds which inhibit the vitronectin receptor and are useful for treatment of inflammation, cancer and cardiovascular disorders, such as atherosclerosis and restenosis, and diseases wherein bone resorption is a factor, such as osteoporosis. In particular, the present invention relates to a novel process for preparing (±)-3-oxo-8-{[3-(pyridin-2-ylamino)propyl]oxy}-2-(2,2,2-trifluoroethyl)-2,3,4,5-tetrahydro-1H-2-benzazepine-4-acetic acid, (R)-3-oxo-8-{[3-(pyridin-2-ylamino)propyl]oxy}-2-(2,2,2-trifluoroethyl)-2,3,4,5-tetrahydro-1H-2-benzazepine-4-acetic acid and (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid or a pharmaceutically acceptable salt thereof.

10 Claims, 1 Drawing Sheet

Figure 1

Scheme 4

PROCESS

This application is a 371 of International Application No. PCT/US2009/036261, filed 6 Mar. 2009, which claims the benefit of U.S. Provisional Application No. 61/034,344, filed 6 Mar. 2008, which are incorporated herein in their entireties.

FIELD OF THE INVENTION

The present invention generally relates to a novel process for preparing vitronectin receptor antagonist compounds having a benzodiazepinyl core structure.

In particular, the present invention relates to a novel process for preparing (±)-3-oxo-8-{[3-(pyridin-2-ylamino)propyl]oxy}-2-(2,2,2-trifluoroethyl)-2,3,4,5-tetrahydro-1H-2-benzazepine-4-acetic acid, (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid, (R)-3-oxo-8-{[3-(pyridin-2-ylamino)propyl]oxy}-2-(2,2,2-trifluoroethyl)-2,3,4,5-tetrahydro-1H-2-benzazepine-4-acetic acid, or a pharmaceutically acceptable salt thereof.

This invention relates to the preparation of pharmaceutically active compounds which inhibit the vitronectin receptor and are useful for treatment of inflammation, cancer and cardiovascular disorders, such as atherosclerosis and restenosis, and diseases wherein bone resorption is a factor, such as osteoporosis.

BACKGROUND OF THE INVENTION

U.S. Pat. No. 6,825,188 B2 to Callahan et al., which is hereby incorporated by reference in its entirety, describes compounds of Formula (I) with a benzazepine core structure, process for preparing and methods for using the aforementioned compounds in the treatment of inflammation, cancer and cardiovascular disorders, such as atherosclerosis and restenosis, and diseases wherein bone resorption is a factor, such as osteoporosis.

One of the processes described in the U.S. Pat. No. 6,825,188 B2 to Callahan et al., which is hereby incorporated by reference in its entirety, utilizes an N-oxide protected pyridine intermediate in the synthesis of the benzazepine core compounds disclosed therein.

A retrosynthetic analysis of the synthesis of compounds described in the U.S. Pat. No. 6,825,188 B2 to Callahan et al., which is hereby incorporated by reference in its entirety, is discussed below.

In particular, a retrosynthetic analysis shown below for preparing compound 1 in Scheme 1 reveals a disconnection that gives previously prepared (±, S or R)-Methyl 2,3,4,5-tetrahydro-8-hydroxy-3-oxo-2-(2,2,2-trifluoroethyl)-1H-2-benzazepine-4-acetate (also known as Methyl (±,4R or 4S)-2,3,4,5-tetrahydro-8-hydroxy-3-oxo-2-(2,2,2-trifluoroethyl)-1H-2-benzazepine-4-acetate (CA-style name)), 2 (see, Wallace, M. D.; McGuire, M. A.; Yu, M. S.; Goldfinger, L.; Liu, L.; Dai, W.; Shilcrat, S. *Organic Process Research and Development* 2004, 8, 738, which is hereby incorporated in reference in its entirety) and pyridyl sidechain 3.

Scheme 1

Compound 1 as shown in Scheme 1 represents each of the following compounds: (±)-3-oxo-8-{[3-(pyridin-2-ylamino)propyl]oxy}-2-(2,2,2-trifluoroethyl)-2,3,4,5-tetrahydro-1H-2-benzazepine-4-acetic acid, (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid, (R)-3-oxo-8-{[3-(pyridin-2-ylamino)propyl]oxy}-2-(2,2,2-trifluoroethyl)-2,3,4,5-tetrahydro-1H-2-benzazepine-4-acetic acid, or a pharmaceutically acceptable salt thereof. However, one of skill in the art would expect that conversion of the alcohol of 3 into a leaving group results in rapid and temperature-dependent cyclization (vide infra) to give 4, which does not act as an electrophile. The acidity of the solution would then dictate the dominant species, 4a or freebase 4b.

The first generation synthesis of Compound 1 shown in Scheme 2 (as disclosed in U.S. Pat. No. 6,825,188 B2 to Callahan et al., which is hereby incorporated by reference in its entirety), relied on the aforementioned retrosynthetic analysis disconnection. In particular, Scheme 2, shows the synthesis scheme as represented by one of the isomers of Compound 1: i.e., (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid, Scheme 2

To circumvent decomposition issues of compound 3 to compound 4 as described above in Scheme 1, the pyridine lone pair was protected as the N-oxide in compound 5. This was accomplished by use of expensive, but commercially available 2-chloropyridine N-oxide Compound 5. The chloride of 5 was first displaced with an amine to generate 6. Treatment with thionyl bromide provided the alkylating agent 7 which was stable and isolable. The phenol 2 was alkylated under basic conditions using 7 which gave 8. Zinc dust removal of the N-oxide to give 9 proved difficult-to-scale due to the density of zinc dust. Issues with adequate mixing gave variable results and differed with reactor configuration. The active principle ingredient (1) could be generated, though, by saponification of methyl ester 9 (48% overall yield from 2).

Three major issues were found in the use of this route: 1) expensive 2-chloro-N-oxide ("N-oxide") (5) is supplied as an aqueous solution and requires a lengthy azeotropic distillation before use; 2) Zn dust reduction of the N-oxide is unpredictable, 3) the N-oxide intermediates are thermally unstable.

In searching for alternative synthetic processes, it was thought that use of a borane protecting group instead of the N-oxide, would provide a viable alternative in light of literature precedents that illustrate the strength of the borane-heterocycle bond.

For instance, the nitrogen lone pair of an oxazole forms surprisingly stable oxazole-borane complexes which requires acidic or Pd treatment for removal. (i.e., see, Monahan, S. D.; Vedejs, E. *J. Org. Chem.*, 1996, 61, 5192 and Zajac, M. A.; Vedejs, E. *Org. Lett.*, 2001, 3, 2451). These complexes are completely stable to chromatography, air and moisture. Additionally, 4-dimethylaminopyridine (DMAP) forms a complex with borane quickly and quantitatively and exhibits similar stability when compared to oxazole-borane complexes (Shapland, P.; Vedejs, E. *J. Org. Chem.*, 2006, 71, 6666.).

Based on the aforementioned examples, it was thought that specific pyridine intermediates used in the synthesis of benzazepine core structure compounds, such as those described in U.S. Pat. No. 6,825,188 B2 to Callahan et al., which is hereby incorporated by reference in its entirety, would exhibit or behave similarly to form stable borane complexes.

However, in considering alternative synthetic routes, while no literature examples were found describing use of borane as a protecting group, there were additional concerns that such a borane protected intermediate would survive extreme reaction conditions, such as treatment with $K_2CO_3$ and heat.

Thus, although the processes disclosed in U.S. Pat. No. 6,825,188 B2 to Callahan et al., which is hereby incorporated by reference in its entirety, produces benzodiazepinyl core structure compounds as defined therein, there is a need to improve processes and find alternative processes for the preparation of such benzodiazepinyl core structure compounds, in light of aforementioned problems associated with the N-oxide protection as discussed above.

It has now been found that benzazepine compounds as discussed herein can be prepared with the use of a borane protecting group with the pyridine starting material, instead of using an N-oxide protecting group with the pyridine starting group to produce such benzazepine compounds efficiently in high yield and high purity. The efficiency of this process and the quality and yield of the benzazepine product compounds are particularly important when preparing said product on a large scale for therapeutic use.

The present invention is directed to overcoming these and other problems encountered in the art.

DESCRIPTION OF THE INVENTION

The present invention relates to a novel process for preparing vitronectin receptor antagonist compounds.

U.S. Pat. No. 6,825,188 B2 to Callahan et al., which is hereby incorporated by reference in its entirety, describes compounds of Formula (I) therein with a benzazepine core structure, process for preparing and methods for using the aforementioned compounds in the treatment of inflammation, cancer and cardiovascular disorders, such as atherosclerosis and restenosis, and diseases wherein bone resorption is a factor, such as osteoporosis.

In light of the above, an embodiment of the present invention generally relates to a novel process for preparing vitronectin receptor antagonist compounds having a benzodiazepinyl core structure defined by Formula (I) as shown below:

or a pharmaceutically acceptable salt thereof, where $R_1$ is $BH_3$ or a lone electron pair; and $R_2$ is hydrogen or methyl and where the process comprises steps of:

[1] treating 2-chloropyridine, 2-fluoropyridine or 2-bromopyridine with 3-aminopropan-ol to form a compound having formula:

at elevated temperatures from about 100° C. to about 160° C. under $N_2$ atmosphere;

[2] converting the compound formed in step [1] to a compound having formula:

by adding thionyl bromide, i.e., $SOBr_2$, at temperatures of about <15° C. to form an intermediate to which is added successively tertiary amines selected from di-isoproplyethyl amine, tri-ethyl amine or 1,8-Diazabicyclo [5.4.0]undec-7-ene (DBU) and the like, followed by addition of borane reagents selected from borane dimethylsulfide ($BH_3$—$SMe_2$), diborane or borane tetrahydrofuran and the like, while maintaining temperatures from about −20° C. to about −70° C.;

[3] reacting the compound formed in step [2] with a compound having formula:

to form a compound of Formula (I).

If Formula (I) is defined where $R_1$ is $BH_3$ and $R_2$ is methyl (defined as Compound 13 in Scheme 3 below):

then the compound formed in step [2] is reacted with i.e., methyl 2,3,4,5-tetrahydro-8-hydroxy-3-oxo-2-(2,2,2-trifluoroethyl)-1H-2-benzazepine-4-acetate (also equivalent chemical name—methyl (4S)-2,3,4,5-tetrahydro-8-hydroxy-3-oxo-2-(2,2,2-trifluoroethyl)-1H-2-benzazepine-4-acetate) in the presence of tetrabutyl ammonium iodide, i.e., $Bu_4NI$, and a suspension of bases selected from potassium carbonate ($K_2CO_3$), phosphazine, 1,8-Diazabicyclo[5.4.0]undec-7-ene (DBU), or cesium carbonate ($Cs_2CO_3$.) at temperatures up to about 50° C., which is followed by successive treatment with varying equivalents of hydrochloric acid, HCl, to obtain the compound when Formula (I) $R_1$ is a lone electron pair; and $R_2$ is methyl (identified as Compound 14 in Scheme 3 below), which is subsequently followed by treatment with varying equivalents of sodium hydroxide, NaOH, (i.e., to saponifying the ester moiety of Compound 14) to obtain the compound when Formula (I) is defined as $R_1$ is a lone electron pair; and $R_2$ is methyl (i.e., identified above as Compound 1 in Scheme 3 below; for specific example reaction conditions/reagent amounts refer to Example Section)

Compounds of Formula (I) of the present invention have one chiral center, unless specified, this invention includes the racemate or each unique nonracemic compound which may be synthesized and resolved by conventional techniques.

In another embodiment, the present invention relates to a process for preparation of a compound of Formula (IA):

or a pharmaceutically acceptable salt thereof, where: $R_1$ is $BH_3$ or a lone electron pair; and $R_2$ is hydrogen or methyl, and which comprises steps of:

[1] treating 2-chloropyridine, 2-fluoropyridine or 2-bromopyridine with 3-aminopropanol to form a compound having formula:

at elevated temperatures from about 100° C. to about 160° C. under $N_2$ atmosphere;

[2] converting the compound formed in step [1] to a compound having formula:

by adding thionyl bromide, i.e., $SOBr_2$, at temperatures of about <15° C. to form an intermediate, to which is added successively tertiary amines selected from di-isoproplyethyl amine, tri-ethyl amine or 1,8-Diazabicyclo [5.4.0]undec-7-ene (DBU) and the like followed by addition of borane reagents selected from borane dimethylsulfide ($BH_3$—$SMe_2$), diborane or borane tetrahydrofuran and the like, while maintaining temperatures from about −20° C. to about −70° C.;

[3] reacting the compound formed in step [2] with a compound having formula:

to form a compound of Formula (I) as obtained under reaction conditions defined above.

In one embodiment, a compound of Formula (I) of the present invention is represented by the (S) configuration of the formula (I) compounds. In particular, compounds synthesized by a process of the present invention, include, but are not limited to:

(±)-3-oxo-8-{[3-(pyridin-2-ylamino)propyl]oxy}-2-(2,2,2-trifluoroethyl)-2,3,4,5-tetrahydro-1H-2-benzazepine-4-acetic acid;

(R)-3-oxo-8-{[3-(pyridin-2-ylamino)propyl]oxy}-2-(2,2,2-trifluoroethyl)-2,3,4,5-tetrahydro-1H-2-benzazepine-4-acetic acid;

(S)-3-oxo-8-{[3-(pyridin-2-ylamino)propyl]oxy}-2-(2,2,2-trifluoroethyl)-2,3,4,5-tetrahydro-1H-2-benzazepine-4-acetic acid; or a pharmaceutically acceptable salt thereof.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic, methanesulfonic and the like. Certain of the compounds form inner salts or zwitterions which may be acceptable.

Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$, $NH_4^+$ and the like are representative specific examples of cations present in pharmaceutically acceptable salts.

Compounds of the present invention may be prepared in accordance with the representive synthetic description discussed below. In particular, synthesis of (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid; derivatives thereof or a pharmaceutically acceptable salt thereof is shown in the Scheme 3.

Typically a novel process of the present invention to produce a compound of Formula (I) is carried out in four stages starting with inexpensive and commercially available 2-chloro pyridine, 10 (see, Scheme 3). While Scheme 3 exemplifies use of 2-chloropyridine, note that also suitable for use in the present invention are other halogen substituted pyridines, such as, but not limited to 2-fluoropyridine or 2-bromopyridine and the like.

Stage 4, aq. HCl, then NaOH
75% over 2 steps

R1 = BH$_3$, R2 = CH$_3$, 13
R1 = lone pair, R2 = H, 1
R1 = lone pair, R2 = CH$_3$, 14

The chloride of 2-chloropyridine is first displaced with amino propanol to generate crystalline, 3-(2-pyridinylamino)-1-propanol, 3, in 74% yield. Treatment with thionyl bromide gives the hydrobromide salt 11 in situ. Neutrallization of 11 with excess iPr$_2$NEt in the presence of borane dimethyl sulfide traps the freebased alkyl bromide as crystalline borane adduct 12. Note that: other tertiary amines conventionally known in the art are suitable for use in the present invention, such as, but not limited to di-isoproplyethyl amine, tri-ethyl amine or 1,8-Diazabicyclo[5.4.0]undec-7-ene (DBU) and the like. Also, other borane reagents conventionally known in the art are also suitable for use in the present invention, such as, but not limited to borane reagents selected from borane dimethylsulfide (BH$_3$—SMe$_2$), diborane or borane tetrahydrofuran and the like.

Fortunately, 12 behaved similarly to the literature examples and was completely water and oxygen stable. Alkylation of (−)-Methyl 2,3,4,5-tetrahydro-8-hydroxy-3-oxo-2-(2,2,2-trifluoroethyl)-1H-2-benzazepine-4-acetate (also equivalent chemical name—Methyl (4S)-2,3,4,5-tetrahydro-8-hydroxy-3-oxo-2-(2,2,2-trifluoroethyl)-1H-2-benzazepine-4-acetate) 2, with 12 was carried out in refluxing MeCN with K$_2$CO$_3$ (It is interesting to note that treatment of 2 with 4 under acidic or basic conditions gives no trace of desired product). The resulting crude product after workup was first treated with 1.1 equivalents of HCl (aqueous, concentrated) to remove the borane protecting group and then with sodium hydroxide to saponify the ester. After adjusting the pH to 5-5.5, 1 crystallized out of solution in 75% yield over the two stages.

During the course of synthetic investigations, the stability of 11 in the presence of iPr$_2$NEt was studied (see, Scheme 4).

Figure 1:
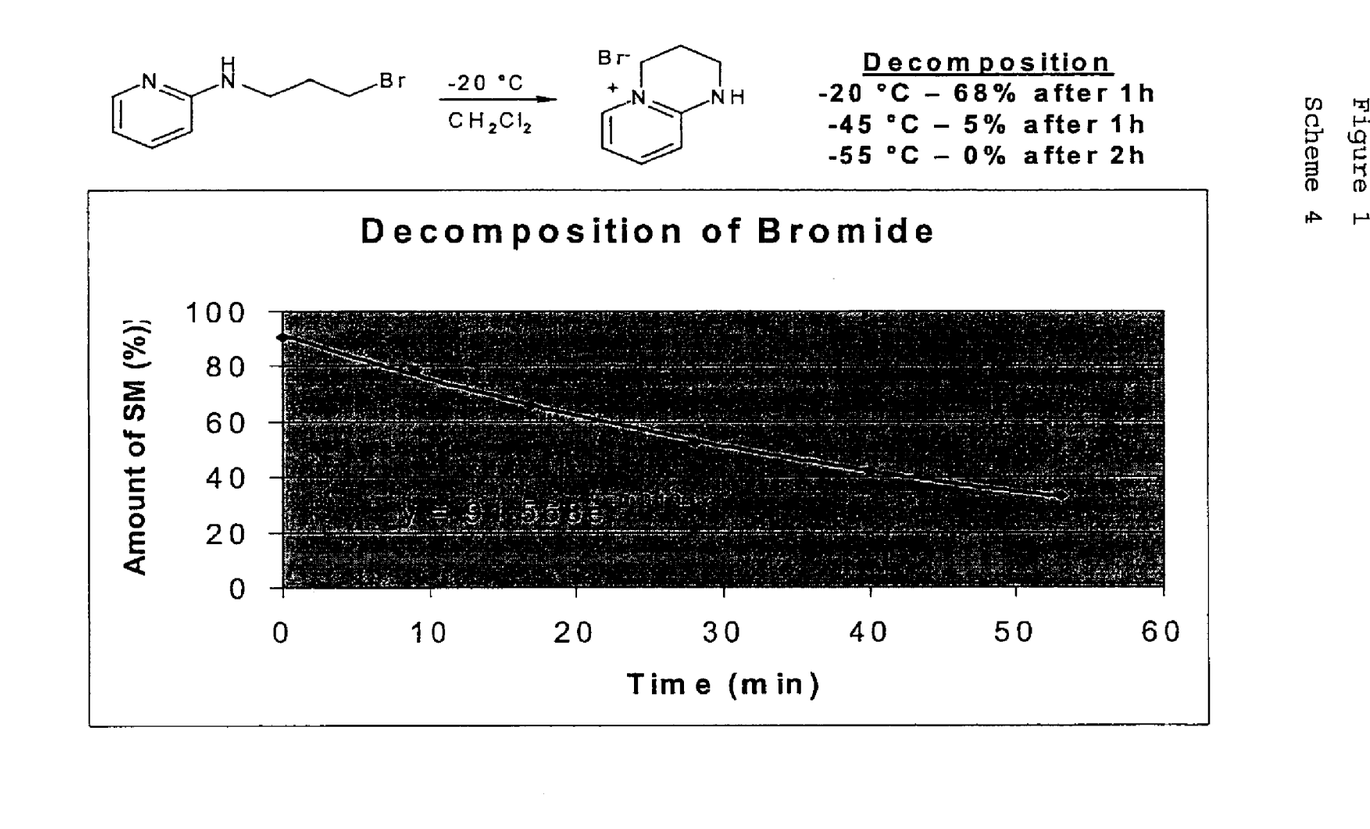
FIG. 1 is directed to Scheme 4, which relates to the Decomposition of Bromide: Stability of 11 in the presence of $iPr_2Net$.

When 11 was treated with two equivalents of base at −55° C., no decomposition was observed after two hours. At −45° C., 5% loss was observed after one hour whereas at −20° C., 68% had cyclized after one hour. This gives a clear indication that cyclization of 11 will occur before alkylation of 2 under basic conditions and that in stage 2 (scheme 3), basification of 11 must occur either in the presence of the borane source or at a temperature <−55° C. (The freebase of 11 reacts faster with borane dimethylsulfide than it does to form 4). The decomposition of 11 at −20° C. is shown graphically in scheme 4. Additionally, the exponential decay equation that fits the data is shown above.

In conclusion, a novel four stage process that produces 1, 13 and 14 from 2 and 10. The new process circumvents all of the issues with the N-oxide in the previous route. As part of the new route, a novel protecting group for pyridine was developed. Thereafter, pharmaceutically acceptable salts may be prepared as described above.

The invention is illustrated by the following examples. The examples are not intended to limit the scope of this invention as defined hereinabove and as claimed hereinbelow.

EXAMPLES

Example 1

Preparation of (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid or a pharmaceutically acceptable salt thereof

[1] Process Stage 1

Preparation of 3-(2-Pyridinylamino)-1-Propanol 2-chloropyridine
$C_5H_4ClN$
113.55 g/mol 3-aminopropan-1-ol
$C_3H_9NO$
75.11 g/mol
d = 0.982 g/mL
2.2 equiv

3-(2-pyridinylamino)-1-propanol
$C_8H_{12}N_2O$
152.2 g/mol

3-aminopropan-1-ol hydrochloride
111.57 g/mol
·HCl

Charge 2-chloropyridine (1.0 equiv) and 3-aminopropan-1-ol (2.2 equiv, 1.5 volumes, 1.5 wt equiv) and mix thoroughly. Purge oxygen from the system by applying vacuum (ca −10 psi) to the system and backfilling with nitrogen three times. Heat the solution to 150° C. and hold for 13-16 h under a nitrogen atmosphere. The light yellow to yellow reaction mixture is then cooled to 18-23° C. and water (1.0 volume, 1.0 wt equiv) is added. Extract the mixture three times with i-PrOAc (3×5.0 volumes, 3×4.4 wt equiv). Combine the organic extracts and wash with water (0.5 volumes, 0.5 wt equiv). Concentrate the i-PrOAc solution in vacuo to minimum stir. Tert-butyl methyl ether (5.0 volumes, 3.7 wt equiv) is used to dissolve the residual oil. Add seed crystals (0.1 wt %) of the pure product and hold at 18-23 for 5 h. Cool the mixture to 0-5° C. and hold for 1-2 h. Isolate the crystalline product by filtration and wash twice with tent-butyl methyl ether (2×2 volumes, 2×1.5 wt equiv) at 5-10° C. Dry 3-(2-pyridinylamino)-1-propanol at 25-30° C. under reduced pressure. Percent yield range observed: 60-70%.

[2] Process Scheme Stage 2

Preparation of N-(3-Bromopropyl)-2-Pyridinamine-1-Boride (i.e., Borane Protected Intermediate 12—Identified in Scheme 3)

Charge 3-(2-pyridinylamino)-1-propanol (1.0 equiv) followed by methylene chloride (5.0 volumes). Mix the contents of the reactor thoroughly for 10 minutes. Cool the solution to 0-5° C. Add thionyl bromide (1.0 equiv) slowly over 5-15 minutes in order to keep the internal temperature <15° C. Warm the yellow mixture to 20-25° C. and hold for 1.5-2 h under a nitrogen atmosphere. Concentrate the solution in vacuo to minimum stir with the jacket temperature at ca. 40° C. and add methylene chloride (5.0 volumes). Cool the solution to −60 to −70° C. and add diisopropylethyl amine (1.1 equiv) directly to the reaction mixture (dip tube) while maintaining the internal temperature below −55° C. Directly after addition is complete, borane dimethylsulfide complex (1.1 equiv) is added directly to the reaction mixture (dip tube) over <25 minutes. The temperature of the mixture is kept below −50° C. during addition. Warm the solution to 10-15° C. and add a saturated aqueous solution of sodium bicarbonate (5.0 volumes) and water (5.0 volumes), mix thoroughly. Collect the organic layer and extract the aqueous layer with methylene chloride (5.0 volumes). Concentrate the combined organic layers in vacuo to minimum stir. At no point during this concentration should the jacket temperature be above 25° C. Add methanol (7.0 volumes) to dissolve/suspend the mixture and stir for 15 minutes. Concentrate the mixture to 5-6 volumes to remove any residual methylene chloride. Cool the mixture to 5-10° C. and isolate the resulting solid by filtration. Wash the solid with cold (~5° C.) methanol (2×2.5 volumes). The wet product is dried at 20-25° C. under reduced pressure.
$^1$H NMR (300 MHz, CDCl$_3$, ppm) δ 8.19 (1H, d, J=8.7 Hz) 7.69-7.61 (1H, m) 6.71 (1H, d, J=5.1 Hz) 6.65-6.59 (1H, m) 6.33 (1H, br. s) 3.58-3.50 (4H, m) 2.24 (2H, p, J=6.0 Hz) 2.80-1.50 (3H, br. m). Percent yield range observed: 70-80%

[3] Process Stage 3

Preparation of (S)-3-oxo-8-{[3-(1-Boro-pyridin-2-ylamino)propyl]oxy}-2-(2,2,2-trifluoroethyl)-2,3,4,5-tetrahydro-1H-2-benzazepine-4-acetate (i.e., Borane Protected Compound 12 From Scheme 3

C$_{23}$H$_{29}$F$_3$N$_3$O$_4$B
MW 479.3
1.0 equiv

+

KHCO3 (1.0 equiv)
KBr (1.0 equiv)
Bu4N I (0.05 equiv)

Add (−)-Methyl 2,3,4,5-tetrahydro-8-hydroxy-3-oxo-2-(2,2,2-trifluoroethyl)-1H-2-benzazepine-4-acetate (also equivalent chemical name—Methyl (4S)-2,3,4,5-tetrahydro-8-hydroxy-3-oxo-2-(2,2,2-trifluoroethyl)-1H-2-benzazepine-4-acetate) (1.0 equiv) to a suspension of potassium carbonate (4.0 equiv) in acetonitrile (5.0 volumes, 3.9 wt equiv) at 18-23° C. Add 3-(2-pyridinylamino)-1-propylbromide hydrobromide (1.2 equiv) and tetrabutylammonium iodide (0.05 equiv); stir the mixture vigorously and heat to 49-52° C. After 16-24 h, cool the mixture to 18-23° C. and concentrate to minimum stir. Add TBME (10 volumes, 7.4 wt equiv) and mix thoroughly. Add 10 volumes of water and mix thoroughly. Collect the TBME layer and backextract the water layer with 10 volumes of TBME. Wash the pooled TBME with 5 volumes of water. Collect the TBME layer, concentrate to minimum stir and add methanol (10 volumes, 7.9 wt equiv). Concentrate to minimum stir. This solution is then used directly in the next step. Percent yield range observed: 100% assumed.

[4] Process Scheme Stage 4

Preparation of: (S)-3-oxo-8-{[3-(pyridin-2-ylamino)propyl]oxy}-2-(2,2,2-trifluoroethyl)-2,3,4,5-tetrahydro-1H-2-benzazepine-4-acetate and Final Product (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid C$_{23}$H$_{29}$F$_3$N$_3$O$_4$B
MW 479.3
1.0 equiv HCl (1.2 equiv) / MeOH

-continued

Dilute the methanol solution of starting material (100% assumed yield on the previous stage) up to 7 volumes with methanol. Cool to 0-5° C. and add concentrated hydrochloric acid (1.2 equiv) while maintaining the temperature <15° C. The mixture gives off $H_2$ upon adding the acid. Warm the mixture to 20-25° C. and hold for up to 3 hours. Cool to 0-5° C. and add 3M NaOH (7.0 equiv) while maintaining the temperature below 15° C. Warm the mixture to 20-25° C. and hold for up to 3 hours. Add enough concentrated hydrochloric acid (~4.8 equiv) to bring the pH to 6.1-6.5 while maintaining the temperature <25° C. Hold for 16-24 h, during which time 1 precipitates out of solution. Isolate 1 by filtration and wash with water (2×5 volumes). Dry the solid product in a vacuum oven at 50-60° C. for up to 12 hours. Percent yield range observed: 75-85% from 2 (over 2 stages)

It is to be understood that the invention is not limited to the embodiments illustrated hereinabove and the right to the illustrated embodiments and all modifications coming within the scope of the following claims is reserved.

What is claimed is:
1. A process for preparation of a compound of Formula (I):

a pharmaceutically acceptable salt thereof, wherein: $R_1$ is $BH_3$ or a lone electron pair; and $R_2$ is hydrogen or methyl, which comprises steps of:
[1] treating 2-chloropyridine, 2-fluoropyridine or 2-bromopyridine with 3-aminopropanol to form a compound having formula:

[2] converting the compound formed in step [1] to a compound having formula:

[3] reacting the compound formed in step [2] with a compound having formula:

to form a compound of Formula (I).
2. The process according to claim 1, wherein the compound of Formula (I) is 3. The process according to claim 1, wherein the compound of Formula (I) is

4. The process according to claim 1, wherein the compound of Formula (I) is

5. The process according to claim 1, wherein the compound of Formula (I) is selected from:
- (±)-3-oxo-8-{[3-(pyridin-2-ylamino)propyl]oxy}-2-(2,2,2-trifluoroethyl)-2,3,4,5-tetrahydro-1H-2-benzazepine-4-acetic acid;
- (R)-3-oxo-8-{[3-(pyridin-2-ylamino)propyl]oxy}-2-(2,2,2-trifluoroethyl)-2,3,4,5-tetrahydro-1H-2-benzazepine-4-acetic acid;
- (S)-3-oxo-8-{[3-(pyridin-2-ylamino)propyl]oxy}-2-(2,2,2-trifluoroethyl)-2,3,4,5-tetrahydro-1H-2-benzazepine-4-acetic acid; or a pharmaceutically acceptable salt thereof.

6. A process for preparation of a compound of Formula (IA):

or
a pharmaceutically acceptable salt thereof,
wherein: $R_1$ is $BH_3$ or a lone electron pair; and $R_2$ is hydrogen or methyl, which comprises steps of:
[1] treating 2-chloropyridine, 2-fluoropyridine or 2-bromopyridine with 3-aminopropanol to form a compound having formula:

[2] converting the compound formed in step [1] to a compound having formula:

[3] reacting the compound formed in step [2] with a compound having formula:

to form a compound of Formula (I).

7. The process according to claim 6, wherein in the compound of Formula (IA), $R_1$ is a lone electron pair and $R_2$ is hydrogen.

8. The process according to claim 6, wherein the compound of Formula (IA) is 9. The process according to claim 6, wherein the compound of Formula (IA) is 10. The process according to claim 6, wherein the compound of Formula (IA) is

* * * * *